(12) United States Patent
Cimiluca et al.

(10) Patent No.: US 9,078,824 B2
(45) Date of Patent: Jul. 14, 2015

(54) COMPOSITION AND METHOD OF STABILIZED SENSITIVE INGREDIENT

(75) Inventors: Paul Alfred Cimiluca, Cincinnati, OH (US); Sonsoles Arnal, La Lagunita (VE); Jorge Zambrano, La Boyera (VE)

(73) Assignee: The Procter & Gamble Company, Cincinnati, OH (US)

( * ) Notice: Subject to any disclaimer, the term of this patent is extended or adjusted under 35 U.S.C. 154(b) by 808 days.

(21) Appl. No.: 12/235,711

(22) Filed: Sep. 23, 2008

(65) Prior Publication Data

US 2009/0082316 A1 Mar. 26, 2009

Related U.S. Application Data

(60) Provisional application No. 61/042,350, filed on Apr. 4, 2008, provisional application No. 60/995,019, filed on Sep. 24, 2007.

(51) Int. Cl.

| | |
|---|---|
| A61K 9/14 | (2006.01) |
| A61K 9/20 | (2006.01) |
| A61K 9/48 | (2006.01) |
| A61K 31/60 | (2006.01) |
| C08J 3/20 | (2006.01) |
| C08K 5/00 | (2006.01) |
| C08L 3/02 | (2006.01) |
| A61K 9/16 | (2006.01) |
| C08L 1/02 | (2006.01) |

(52) U.S. Cl.
CPC ............ *A61K 9/2013* (2013.01); *A61K 9/2054* (2013.01); *A61K 9/2059* (2013.01); *A61K 31/60* (2013.01); *C08J 3/20* (2013.01); *C08K 5/0008* (2013.01); *C08L 3/02* (2013.01); *A61K 9/1694* (2013.01); *C08J 2303/02* (2013.01); *C08L 1/02* (2013.01)

(58) Field of Classification Search
None
See application file for complete search history.

(56) References Cited

U.S. PATENT DOCUMENTS

| | | | |
|---|---|---|---|
| 3,453,368 A | | 7/1969 | Magid |
| 3,480,185 A | | 11/1969 | Steinberg et al. |
| 5,047,246 A | * | 9/1991 | Gallian et al. ............... 424/464 |
| 5,409,709 A | | 4/1995 | Ozawa et al. |
| 5,500,227 A | | 3/1996 | Oshlack et al. |
| 5,674,522 A | | 10/1997 | Shah et al. |
| 6,024,982 A | | 2/2000 | Oshlack et al. |
| 2001/0026809 A1 | | 10/2001 | Oshlack et al. |
| 2001/0043959 A1 | * | 11/2001 | Gelber et al. ................. 424/764 |
| 2001/0044410 A1 | | 11/2001 | Gilber et al. |
| 2003/0138495 A1 | | 7/2003 | Jepsen |
| 2004/0062805 A1 | | 4/2004 | Vandecruys et al. |
| 2004/0101494 A1 | | 5/2004 | Scott et al. |
| 2005/0153978 A1 | * | 7/2005 | Alberti et al. ............ 514/254.06 |
| 2005/0232987 A1 | | 10/2005 | Srinivasan et al. |
| 2006/0127473 A1 | * | 6/2006 | Nichols ........................ 424/464 |
| 2006/0141031 A1 | | 6/2006 | Nelson et al. |
| 2007/0054023 A1 | * | 3/2007 | Bingley et al. ................ 426/548 |
| 2007/0141147 A1 | | 6/2007 | Heil et al. |
| 2007/0160695 A1 | | 7/2007 | Clouatre |
| 2007/0196481 A1 | * | 8/2007 | Amidon et al. ............... 424/468 |
| 2009/0047343 A1 | * | 2/2009 | Huang et al. .................. 424/464 |
| 2010/0047345 A1 | * | 2/2010 | Crowley et al. ............... 424/468 |

FOREIGN PATENT DOCUMENTS

| | | |
|---|---|---|
| EP | 0305051 A | 3/1989 |
| EP | 1757274 | 2/2007 |
| JP | 08 325145 | 5/1995 |
| JP | 11 335279 | 5/1998 |
| JP | 2001/261580 | 3/2000 |
| JP | 2004/067516 | 8/2002 |
| WO | WO 92/21328 A | 12/1992 |
| WO | WO 98/18610 A | 5/1998 |
| WO | WO 00/59477 A | 10/2000 |
| WO | WO 0059477 A1 * | 10/2000 |
| WO | WO 01/25414 A | 4/2001 |
| WO | WO 01/72318 A | 10/2001 |
| WO | WO 03/089007 | 10/2003 |
| WO | WO 2004/010998 A | 2/2004 |
| WO | WO 2005/063199 | 7/2005 |
| WO | WO 2005/063200 A | 7/2005 |
| WO | WO 2006/022996 A | 3/2006 |

OTHER PUBLICATIONS

Sanchez, L., et al., "Gelatinized/freeze-dried starch as excipient in sustained release tablets," International Journal of Pharmaceutics, Elsevier BV, NL, vol. 115, Jan. 1, 1995, pp. 201-208.
International Search Report.

\* cited by examiner

*Primary Examiner* — Susan Tran
(74) *Attorney, Agent, or Firm* — Alexandra S. Anoff

(57) ABSTRACT

The present invention comprises a method of achieving ingredient stabilization in a composition comprising the steps of: combining a pregelatinized starch with at least one sensitive ingredient; adsorbing said sensitive ingredient onto the pregelatinized starch; and wherein said sensitive ingredient is evenly distributed throughout said pregelatinized starch.

25 Claims, No Drawings

COMPOSITION AND METHOD OF STABILIZED SENSITIVE INGREDIENT

CROSS REFERENCE TO RELATED APPLICATIONS

This application claims the benefit of U.S. Provisional Application No. 61/042,350 filed Apr. 4, 2008 and U.S. Provisional Application No. 60/995,019, filed on Sep. 24, 2007.

FIELD OF THE INVENTION

The present invention relates to a method of achieving ingredient stabilization in a composition comprising the steps of: combining a pregelatinized starch with at least one sensitive ingredient; adsorbing said sensitive ingredient onto the pregelatinized starch; and wherein said sensitive ingredient is evenly distributed throughout said pregelatinized starch.

BACKGROUND OF THE INVENTION

Many biologically important compounds lose activity if exposed to heat, water and/or oxygen. Such compounds include vitamins, herbal remedies, antioxidants, carotenoids, polyphenols, minerals, fatty acids, amino acids, enzymes, probiotics analgesics, anticholinergics, antihistamines, anti-inflammatories, antipyretics, antitussives, antivirals, decongestants, expectorants, mucolytics, and prebiotics. Numerous attempts have been made in an effort to stabilize these compounds so that the activity of the compounds is maintained over longer periods of time upon exposure to heat, water and/or oxygen. Certain of these methods have focused on coating of the compounds with a protective material, including gelatin and alginate. Protecting the compounds against degradation is not the only concern, however. The protected compounds must also be available for biological absorption upon oral ingestion. These two purposes are inherently conflicting in that known methods of protection of the compounds during processing and storage have also limited or prevented absorption of the compounds so that less of the biologically important compound is effectively delivered to the ingesting mammal.

The only reliable option to be able to deliver the compounds is to over-formulate the labile components that are included in the composition. This over-formulation adds unnecessary expense and does not guarantee product performance. In the case of a tablet or capsule with low level components, the tablet weight is very high relative to the amount of low-level active labile ingredients. This presents a problem in that it is difficult to uniformly disperse the minor actives in the massive tablet or capsule.

It is therefore an object of the present invention to provide a composition and method of stabilizing sensitive ingredients, preferably via a pregelatinized starch, in which all of the sensitive ingredients in a composition are stable and maintain the sensitive ingredients activity in the presence of heat, water and/or oxygen, are still available for biological absorption upon oral ingestion, and are evenly distributed throughout the pregelatinized starch.

SUMMARY OF THE INVENTION

The present invention relates to a method of achieving ingredient stabilization in a composition comprising the steps of: combining a pregelatinized starch with at least one sensitive ingredient; adsorbing said sensitive ingredient onto the pregelatinized starch; and wherein said sensitive ingredient is evenly distributed throughout said pregelatinized starch.

The present invention further relates to a composition comprising: a pregelatinized starch; at least one sensitive ingredient selected from the group consisting of carotenoid, rosemary, rosemary extract, caffeic acid, coffee extract, tumeric extract, curcumin, blueberry extract, grapeseed extract, rosemaric acid, tea extract, antioxidant, amino acid, enzyme, prebiotic, probiotic Vitamin A, Vitamin B, Vitamin C, Vitamin D, andrographis extract, 1-tryptophan, Allium sativum, analgesics, anticholinergics, antihistamines, anti-inflammatories, antipyretics, antitussives, antivirals, decongestants, expectorants, mucolytics, and combinations thereof; wherein said sensitive ingredient is adsorbed onto the pregelatinized starch; and wherein said sensitive ingredient is evenly distributed throughout said pregelatinized starch.

DETAILED DESCRIPTION OF THE INVENTION

The present invention relates to a method of achieving ingredient stabilization in a composition.

The term "sensitive ingredient" as used herein refers to an ingredient that undergoes non-hydrolytic decomposition reactions accelerated by water and/or low-level actives that adsorb onto the surface of a pregelatinized starch. Preferably the sensitive ingredient is one that undergoes oxidation, thermal degradation, rearrangement or other reactions promoted by the presence of water.

The term "oral compositions" as used herein refers to compositions in a form that is deliverable to a mammal in need. Nonlimiting examples include liquid compositions, nasal compositions, beverage, supplemental water, pills, soft gels, tablets, two layered tablets, capsules, gel compositions, and combinations thereof. Nasal compositions, liquid compositions, gel compositions can be in a form that is directly deliverable to the airway passages from the nose and mouth. These compositions can be delivered via droppers, pump sprayers, irrigation devices, pressurized sprayers, atomizers, air inhalation devices and other packaging and equipment.

All weights, measurements and concentrations herein are measured at 25° C. on the composition in its entirety, unless otherwise specified.

These and other limitations of the compositions and methods of the present invention, as well as many of the optional ingredients suitable for use herein, are described in detail hereinafter.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The composition and methods of the present invention can comprise, consist of, or consist essentially of, the essential elements and limitations of the invention described herein, as well as any additional or optional ingredients, components, or limitations described herein or otherwise useful in compositions intended for use by a mammal, preferably human use.

Composition

The present invention is a composition and methods of stabilizing sensitive ingredients, preferably via a pregelatinized starch, in which all of the sensitive ingredients in a composition are stable and maintain the sensitive ingredients activity in the presence of heat, water and/or oxygen, are still available for biological absorption upon oral ingestion, and are evenly distributed throughout the pregelatinized starch.

The preferred pH range of the composition is from about 1 to about 7, from about 2 to about 6.5, from about 2 to about 5 and from about 2.6 to about 4.5.

The composition of the present invention is preferably an oral composition and can be liquid or semi-liquid, or gel or nasal compositions, beverage, supplemental water, pills, tablets, twp layered tablet, soft gels or capsules.

Sensitive Ingredients

The composition of the present invention comprises a sensitive ingredient wherein the sensitive ingredient is stabilized by combining a pregelatinized starch with at least one sensitive ingredient; adsorbing said sensitive ingredient onto the pregelatinized starch; and wherein said sensitive ingredient is evenly distributed throughout said pregelatinized starch.

The composition comprises from about 1% to about 20% of a sensitive ingredient, by weight of the composition, alternatively from about 0.5% to about 15%, alternatively from about 1% to about 10%, alternatively from about 1.5% to about 5%, alternatively from about 2% to about 4% of sensitive ingredient, by weight of the composition.

Nonlimiting Examples of sensitive ingredients includes, Vitamin C, Vitamin B, Vitamin D, carotenoid, rosemary, rosemary extract, caffeic acid, coffee extract, tumeric extract, curcumin, blueberry extract, grapeseed extract, rosemaric acid, tea extract, antioxidant, amino acid, enzyme, prebiotic, probiotic, Vitamin A, andrographis extract, 1-tryptophan, Allium sativum, analgesics, anticholinergics, antihistamines, anti-inflammatories, antipyretics, antitussives, antivirals, decongestants, expectorants, mucolytics, and combinations thereof.

The preferred form of Vitamin C for use in the composition is as ascorbic acid or the equivalent of a salt of ascorbic acid or the equivalent of a derivative of ascorbic acid. The vitamin C may either be in an immediate release form or a sustained release form.

Vitamin A and carotene can be obtained from either animal or vegetable sources. The vitamin A can be in the form of vitamin A, retinol, retinyl palmitate, retinyl acetate, retinyl propriante, beta-carotene, alpha carotene, beta-cryptoxanthin, and mixtures thereof.

Nonlimiting examples of Vitamin D suitable for the present invention include Vitamin D3 (cholecalciferol), Vitamin D2 (ergocalciferol) and combinations thereof. Additional, non-limiting examples also include metabolites of Vitamin D, including calcidiol, calcitriol, and combinations thereof. The Vitamin D, including cholecalciferol, ergocalciferol, calcidiol and calcitriol, may be derived from synthetic or natural sources. Vitamin D, including cholecalciferol and calcitriol, may be sourced from an extract of solanum glaucophyllum (malacoxylon), trisetum flavescens (goldhafer) or cestrum diurnum. Both the pure, Vitamin D and/or glycosides of the Vitamin D, may be used.

Example decongestants include: oxymetazoline, phenylephrine, xylometazoline, naphazoline, 1-desoxyephedrine, ephedrine, propylhexedrine, pseudoephedrine, and phenylpropanolamine. Example anticholinergics include: ipratropium, chlorpheniramine, brompheniramine, diphenhydramine, doxylamine, clemastine, and triprolidine. Common analgesics, anti-inflammatories and antipyretics include: ibuprofen, ketoprofen, diclofenac, naproxen, acetaminophen, and aspirin. Example antivirals include: amantidine, rimantidine, pleconaril, zanamivir, and oseltamivir. Examples of antitussives include codeine, dextromethorphan, chlophedianol and levodropropizine. Examples of expectorants include guaifenesin. Examples of mucolytics include ambroxol and N-acetylcysteine. Examples of antihistamines include diphenhydramine, doxylamine, triprolidine, clemastine, pheniramine, chlorpheniramine, brompheniramine, loratadine, cetirizine and fexofenadine.

Tea extract is a polyphenol. Nonlimiting examples of extracts includes *Camellia sinensis*. Nonlimiting sources of tea extract for use in the present invention are black tea, white tea, oolong tea, and/or green tea.

When present, the composition comprises from about $10^6$ to $10^{12}$ cfu of a probiotic, and alternatively from about $10^6$ to $10^{10}$ cfu of a probiotic. The probiotic component can be a lactic acid bacteria. Preferably the probiotic is selected from the group consisting of bacteria of the genera *Bacillus, Bacteroides, Bifidobacterium, Enterococcus* (e.g., *Enterococcus faecium*), *Lactobacillus*, and *Leuconostoc*, and combinations thereof. In another embodiment of the invention, the probiotic is selected from bacteria of the genera *Bifidobacterium, Lactobacillus*, and combinations thereof.

Non-limiting examples of lactic acid bacteria suitable for use herein include strains of *Streptococcus lactis, Streptococcus cremoris, Streptococcus diacetylactis, Streptococcus thermophilus, Lactobacillus bulgaricus, Lactobacillus acidophilus* (e.g. *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum*, and *Pediococcus cerevisiae*, or mixtures thereof, preferably *Lactobacillus salivarius, Bifidobacterium infantis*, or mixtures thereof.

As used herein, the *andrographis* is a plant of the genus *Andrographis*, having a limited number of species within this genus largely present in Asia. Only a few of the species are medicinal. In one embodiment, the plant is of the species *Andrographis paniculata*, which may be referenced as Kalmegh in Ayurvedic medicine.

Coffee extract is a polyphenol. The main constituent of coffee extract is coffeic acid. When coffee extract is present nonlimiting sources of coffee extract include coffee, coffee bean, coffee berry, and/or coffee fruits. When coffeic acid is present nonlimiting sources of coffeic acid include coffee bean, coffee fruits, coffee, tea, berries, rosemary extract, and/or grapes extract.

Turmeric extract is a polyphenol. Turmeric extract is a spice which comprises a main active compound that is curcumin. Curcumin is a bioactive polyphenol plant pigment. Nonlimiting source of turmeric extract for use in the present invention is turmeric.

Blueberry extract is a polyphenol. The blueberry extract is rich in anthocyanins which display antioxidant activity.

Grapeseed extract is a polyphenol. The grape seed extract is rich in procyanidins which display antioxidant activity. Nonlimiting source of grapeseed extract for use in the present invention is grape seed.

A "carotenoid" is a class of pigments occurring in the tissues of higher plants, algae, bacteria and fungi. They are usually yellow to deep red. When a carotenoid is present, the carotenoid is selected from the group consisting of betacarotene, lutein, astaxanthin, zeaxanthin, bixin, lycopene, and mixtures thereof.

Amino acids are the "building Blocks" of the body. Besides building cells and repairing tissue, they form antibodies to combat invading bacteria & viruses; they are part of the enzyme & hormonal system; they build polynucleic acids (RNA & DNA); they carry oxygen throughout the body and participate in muscle activity. When an amino acid is present, the amino acid is selected from the group consisting of Lysine, Taurine, Histidine, Carnosine, Alanine, Cysteine, and mixtures thereof.

When an antioxidant is present, the antioxidant is selected from the group consisting of Vitamin E, CoQ10, and mixtures thereof. Major dietary sources of vitamin E are vegetable oils, margarine and shortening, with nuts, seeds, whole grains and wheat germ providing additional sources. "Vitamin E" includes eight different chemical forms: four tocopherols and four tocotrienols. The most biologically active form of vitamin E is alpha-tocopherol.

In an additional embodiment the sensitive ingredient is encapsulated within a coating before the sensitive ingredient is combined with the pregelatinized starch. The coating aids by providing an additional barrier for sensitive ingredients like Vitamin C and phenylephrine and the coating helps to stabilize the sensitive ingredients upon exposure to heat, water and/or oxygen. Preferably the coating does not contain reducing sugars such as dextrose, fructose, sucrose and combinations thereof. Additionally, the coating aids in preventing the discoloration of the composition caused by sensitive ingredients such as doxylamine. Nonlimiting examples of coatings include cellulose derivatives, cellulose ethers, methyl cellulose, ethylcellulose, carboxymethylcellulose, carboxymethylethylcellulose, hydroxyethyl cellulose, hydroxypropyl cellulose, hydroxypropyl methylcellulose, low viscosity hydroxypropyl cellulose, low viscosity hydroxypropyl methylcellulose, wax or wax like substance, such as carnauba wax, fatty alcohols, hydrogenated vegetable oils, zein, shellac, sucrose, Arabic gum, polyethylene glycol, polyvinylpyrolidone, gelatin, sodium alginate, dextrin, psyllium husk powder, polymethacrylates, anionic polymethacrylates, poly(methacrylic acid, methyl methacrylate) 1:1, mixtures of poly(methacrylic acid, methyl methacrylate) 1:2 and poly(methacrylic acid, methyl methacrylate) 1:1, cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, poly(methacrylic acid, ethyl acrylate) 1:1, and compatible mixtures thereof.

Pregelatinized Starch

The composition comprises pregelatinized starch. It is believed that pregelatinized starch provides benefits in multiple ways. First, it is believed that the pregelatinized starch adsorbs moisture from the atmosphere, or moisture introduced by other raw materials, the starch binds this moisture and makes it unavailable for unwanted chemical reactions. The starch molecule contains many available hydroxyl functions which readily form hydrogen bonds to water molecules trapping these water molecules in a matrix of starch polysaccharide strands. Pregelatinized starch is also stable to deliquescence. That is, it can adsorb large amounts of water without dissolving in this water.

Secondly, it is believed that the pregelatinized starch, which is a fine particulate material, adheres to the sensitive ingredients and pharmaceutical actives which allow them to disperse evenly throughout the pregelatinized starch.

The pregelatinized starch is combined with a sensitive ingredient and the sensitive ingredient is adsorbed onto the pregelatinized starch. Additionally, the sensitive ingredient and the pregelatinized starch can be combined in such a way to form a pre-blend. This pre-blend can be geometrically diluted with the remaining pharmaceutical actives, additional sensitive ingredients, excipients and mixtures thereof, to yield a uniform dispersion throughout the pregelatnized starch and/or the composition. Pregelatinized starch is particularly useful in tablets or capsules with active ingredients that are unstable to moisture because, besides binding moisture, pregelatinized starch is a directly compressible material, it flows well. Additionally, pregelatinized starch quickly adsorbs water and swells, thus disrupting the tablet capsule matrix and leading to disintegration which aids the tablets and capsules disintegrate and release the sensitive ingredients.

In one embodiment the sensitive ingredient is ascorbic acid. It is believed that pregelatinized starch attracts and strongly binds environmental moisture, this moisture is unavailable to participate in the ascorbic acid degradation process. Therefore tablets or capsules containing pregelatinized starch may show zero to low ascorbic acid degradation after a period of time.

In an additional embodiment the sensitive ingredient can be phenylephrine. The phenylephrine reaction with aldehydes is accelerated in the presence of water. It is believed that the ability of pregelatinized starch to bind water is able to suppress this reaction.

The composition comprises from about 5% to about 80% of a pregelatinized starch, by weight of the composition, alternatively from about 8% to about 70%, by weight of the composition, alternatively from about 10% to about 60%, alternatively from about 20% to about 50%, alternatively from about 30% to about 40% of a pregelatinized starch, by weight of the composition.

Nonlimiting examples of pregelatinized starch include pregelatinized potato, wheat or corn starch. Nonlimiting examples of corn starch include Starch®1500, supplied by Colorcon, Instabind IC-820 supplied by Ideal Cures PVT. Ltd., and Lycatab®PGS, supplied from Roquette, as well as, any compendial pregelatinized starch.

Additional Pharmaceutical Active

The compositions of the present invention can comprise a wide range of additional pharmaceutical actives. Nonlimiting examples include antitussives, antihistamines, non-sedating antihistamines, decongestants, expectorants, analgesics, antipyretic anti-inflammatory agents, local anesthetics, anti-inflammatory agents, demulcents, herbal remedies, vitamins, supplements, antioxidants, natural ingredients, minerals, energy boosting ingredients, sleep aids and immune system boosting, tea extract, antioxidant, amino acid, enzyme, prebiotic, probiotic, *andrographis* extract, 1-tryptophan, Allium sativum, anticholinergics, antivirals, mucolytics, and combinations thereof.

Example of decongestants include: oxymetazoline, phenylephrine, xylometazoline, naphazoline, 1-desoxyephedrine, ephedrine, propylhexedrine, pseudoephedrine, and phenylpropanolamine. Example of anticholinergics include: ipratropium, chlorpheniramine, brompheniramine, diphenhydramine, doxylamine, clemastine, and triprolidine. Common analgesics, anti-inflammatories and antipyretics include: ibuprofen, ketoprofen, diclofenac, naproxen, acetaminophen, and aspirin. Example of antivirals include: amantidine, rimantidine, pleconaril, zanamivir, and oseltamivir. Examples of antitussives include codeine, dextromethorphan, chlophedianol and levodropropizine. Examples of expectorants include guaifenesin. Examples of mucolytics include ambroxol and N-acetylcysteine. Examples of antihistamines include diphenhydramine, doxylamine, triprolidine, clemastine, pheniramine, chlorpheniramine, brompheniramine, loratadine, cetirizine and fexofenadine.

Nonlimiting examples of additional pharmaceutical actives include but are not limited to, pyrilamine, promethazine, oxycodone, hydrocodone, carbinoxamine, caffeine, benzonatate, pheniramine, fentanyl, azatedine, desloratadine, carbamazepine, buprenorphine, hydromorphone, indomethacin, oxymorphone, phenol, codeine, mesalamine, dichlophenac, sulindac, beclomethaxone, meloxicam, fenoproten, mometasone, menthol, benzocaine, dipyridamole, methscopolamine, the free and the addition salt forms, chamomile, passion flower, Vitamin C, Vitamin D, B Vitamins, echinacea, melatonin, green tea, curcumin, zinc, selenium, calcium, guarana, probiotics and mixtures thereof.

The compositions of the present invention may comprise an amount of at least one additional pharmaceutical active in the range of about zero (0) mg to about 1,000 mg of each of at least one additional pharmaceutical active, alternatively from about 2.5 mg to about 750 mg, and alternatively from about 5 mg to about 650 mg of each of at least one additional pharmaceutical active, all per dose of the composition.

The compositions of the present invention may comprise an amount of additional pharmaceutical active in the range of about 0% to about 20%, alternatively 0.0001% to about 15%, alternatively from about 0.001% to about 10%, and alternatively from about 0.01% to about 5%, all by weight of the composition.

Excipients

The composition can comprise an excipient. The composition can comprise from about 0.1% to about 99% of the excipient, by weight of the composition, alternatively from about 0.25% to about 70%, alternatively from about 0.5% to about 70%, alternatively from about 2% to about 70%, alternatively from about 3% to about 40%, alternatively from about 5% to about 30%, alternatively from about 6% to about 25% of the excipient, by weight of the composition. Nonlimiting examples of excipients include of microcrystalline cellulose, dicalcium phosphate, stearic acid, magnesium stearate, corn starch, lactose, sodium croscarmellose, sodium starch glycolate, polyvinylpyrrollidone, gelatin and combinations thereof. When the excipient is magnesium stearate, the level of magnesium stearate present is at least 0.1%, alternatively less than about 0.5%, alternatively less than about 0.25%, by weight of the composition. By keeping the level of magnesium stearate at least about 0.1%, aids to prevent darkening of the composition caused by the presence of certain sensitive ingredients such as doxylamine and/or phenylephrine.

Chelating Agent

The composition may comprise a chelating agent. Nonlimiting examples of chelating agents include but are not limited to the salts of disodium and calcium salts of ethylene diamine tetraacetic acid (EDTA), tetrasodium EDTA, sodium hexametaphosphate (SHMP), citric acid, phosporic acid, di(hydroxyethyl)glycine, 8-hydroxyquinoline, and mixtures thereof. Trivalent metal chelating agents such as galactomannans complexed with iron may also be useful.

Wherein the compositions herein comprise a chelaing agent, the compositions may optionally comprise from about 0.0001% to about 1% of the chelating agent, alternatively from about 0.001% to about 0.5%, and alternatively from about 0.01% to about 0.3% of the chelating agent, all by weight of the composition.

Sweeteners

The composition of the present invention may comprise a sweetener to provide sweetness and aid in the taste masking of a pharmaceutical active(s) and/or sensitive ingredients. The sweeteners of the present invention can be artificial sweeteners and/or natural sweeteners. Non-limiting examples of artificial sweeteners are selected from the group consisting of sodium saccharine, acesulfame potassium, sucralose, aspartame, monoammonium glycyrrhizinate, neohesperidin dihydrochalcone, thaumatin, neotame, cyclamates, and mixtures thereof. Nonlimiting examples of natural sweeteners include sucrose, fructose, glucose, glycerin, sorbitol, maltitol, and mannitol and combinations thereof.

Optional Ingredients

The compositions of the present invention can comprise a wide range of optional ingredients. Nonlimiting examples of optional ingredients include antimicrobial metal salts, optional mildness enhancers, optional stabilizers, abrasives, antioxidants, biological additives, chemical additives, colorants, coolants, chelants, denaturants, drug astringents, emulsifiers, external analgesics, film formers, fragrance compounds, humectants, opacifying agents, plasticizers, preservatives, propellants, reducing agents, solvents, foam boosters, hydrotropes, solublizing agents, suspending agents (non-surfactant), a solvent, viscosity increasing agents (aqueous and non-aqueous), sequestrants, vitamins, antioxidants, buffers, keratolytics, and the like, and combinations thereof. Preferably the optional ingredient is selected from the group consisting of solvents, a chelant, a preservative, a fragrance, buffer, antimicrobial metal salts and combinations thereof.

Nonlimiting examples of antimicrobial metal salts include zinc, iron, copper, silver, tin, bismuth, and combinations thereof.

Nonlimiting examples of preservative include but are not limited to benzoalkonium chloride, EDTA, benzyl alcohol, potassium sorbate, parabens, and mixtures thereof.

Unless otherwise specified, the compositions may optionally comprise one or more given optional ingredients at concentrations ranging from about 0.001% to about 99%, alternatively from about 0.01% to about 80%, alternatively from about 0.01% to about 50%, alternatively from about 0.01% to about 10%, all by weight of the composition.

Methods of Use

As used herein, the term "orally administering" with respect to the mammal means that the mammal ingests or is directed to ingest, or does ingest, one or more of the present compositions. Wherein the human is directed to ingest the composition, such direction may be that which instructs and/or informs the human that use of the composition may and/or will provide the relief from the respiratory illness (e.g. symptomatic relief, whether temporary or permanent) for example, relief from congestion. For example, such direction may be oral direction (e.g., through oral instruction from, or example, a physician, pharmacists, or other heath professional), radio or television media (i.e., advertisement), or written direction (e.g., through written direction from, for example a physician, pharmacist, or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a container holding the composition). As used herein, "written" means through words, pictures, symbols, and/or other visible or tactile descriptors, such as Braille. Such information need not utilize the actual words used herein, for example, "respiratory", "illness", or "mammal", but rather use of words, pictures, symbols and the like conveying the same or similar meaning are contemplated within the scope of this invention.

Administration may be on an as-needed or as-desired basis, for example, once-monthly, once-weekly, or daily, including multiple times daily, for example, at least once daily, twice daily, three times daily, or four times daily or more.

The amount of composition administered may be dependent on a variety of factors, including the general quality of health of the mammal, type of mammal, age, gender, or severity of symptoms.

In one embodiment herein, an oral composition is administered to the mammal, that provides in total dosage amounts, per dose, of from about 0.15 to about 180 µg/kg body weight of the mammal, alternatively from about 0.7 to about 40 µg/kg body weight of the mammal, alternatively from about 3 to about 20 µg/kg body weight of the mammal, of sensitive ingredient In one embodiment herein, an oral composition is administered to the mammal, that provides in total dosage amounts, per dose, of from about 10 to about 1500 µg/kg body weight of the mammal, alternatively from about 50 to about 750 µg/kg body weight of the mammal, alternatively from about 100 to about 300 µg/kg body weight of the mammal, of sensitive ingredient.

Method of Making

The compositions of the present invention may be prepared by any known or otherwise effective techniques suitable for providing a composition that provides a therapeutic benefit. In one embodiment the composition is made by combining a sensitive ingredient with the pregelatinized starch. The combined ingredients are passed through a screen into a V-blender and blended until uniform. Additionally one could add to the blend microcrystalline cellulose and continue blending until uniform. Next, the composition is compressed on a tablet press.

In an alternative embodiment, the composition is made by combining a sensitive ingredient with the pregelatinized starch. The combined ingredients are passed through a screen into a V-blender and blended until uniform. Additionally, one could add to the composition and continue blending until uniform. Next, the composition is compressed on a tablet press.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Example No. 1

| Raw Material | % w/w |
| --- | --- |
| Acetaminophen | 54.7 |
| Phenylephrine HCl | 0.8 |
| Dextromethorphan HBr | 1.5 |
| Ascorbic Acid | 9.5 |
| Microcrystalline Cellulose | 15.0 |
| Pregelatinized Starch | 16.5 |
| Stearic Acid | 1.5 |
| Magnesium Stearate | 0.5 |

Example 1 can be made by passing Phenylephrine HCl, Dextromethorphan HBr and Pregelatinized Starch through a 14 mesh screen and blend for 100 revolutions in a V-blender. Next, pass Ascorbic Acid and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press.

Example 2

| Raw Material | % w/w |
| --- | --- |
| Acetaminophen | 54.7 |
| Doxylamine Succinate | 0.9 |
| Dextromethorphan HBr | 2.3 |
| Ascorbic Acid | 19.1 |
| Microcrystalline Cellulose | 9.8 |
| Pregelatinized Starch | 11.2 |
| Stearic Acid | 1.5 |
| Magnesium Stearate | 0.5 |

Example 2 can be made by made by passing Doxylamine Succinate, Dextromethorphan HBr and Pregelatinized Starch through a 14 mesh screen and blend for 100 revolutions in a V-blender. Next, pass Ascorbic Acid and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press.

Example 3

| Raw Material | % w/w |
| --- | --- |
| Bifido Bacterium (Freeze-dried) | 5.0 |
| Pregelatinized Starch | 25.0 |
| Microcrystalline Cellulose | 65.0 |
| Stearic Acid | 5.0 |

Example 3 can be made by passing freeze-dried Bifido Bacterium and Pregelatinized Starch through a 20 mesh screen into a V-blender and blend for 100 revolutions. Next, pass Ascorbic Acid and Microcrystalline Cellulose through a 14 mesh screen into the pregelatinized starch mixture and blend for 100 revolutions to form the composition. Fill the composition into hard gelatin capsules on a capsule-filling machine.

Example 4

| Raw Material | % w/w |
| --- | --- |
| Ibuprofen | 50.00 |
| Phenylephrine HCl | 1.25 |
| Pregelatinized Starch | 10.00 |
| Microcrystalline Cellulose | 38.25 |
| Magnesium Stearate | 0.50 |

Example 4 can be made by passing Phenylephrine HCl and Pregelatinized Starch through a 14 mesh screen and blend for 100 revolutions in a V-blender. Next, pass Ibuprofen and Microcrystalline Cellulose through a 14 mesh screen into the pregelatinized starch mixture and blend for 100 revolutions. Next, Pass Magnesium Stearate through a 20 mesh screen into the pregelatinized mixture and blend for 30 revolutions to form the composition. Compress the composition on a tablet press.

Example 5

| Raw Material | % w/w |
| --- | --- |
| Vitamin E | 3.75 |
| Vitamin C | 25.00 |
| Pregelatinized Starch | 20.00 |
| Sorbitol | 48.25 |
| Stearic Acid | 3.0 |

Example 5 can be made by passing Vitamin E and Pregelatinized Starch through a 14 mesh screen and blend for 100 revolutions in a V-blender. Next, pass Vitamin C and Sorbitol through a 14 mesh screen into the pregelatinized starch mixture and blend for 100 revolutions. Next, Pass Stearic Acid through a 20 mesh screen into the pregelatinized mixture and blend for 30 revolutions to form the composition. Compress the composition on a tablet press.

Example 6

| Raw Material | % w/w |
| --- | --- |
| Directly Compressible Acetaminophen 90% | 53.1113 |
| Phenylephrine Hydrochloride | 0.7781 |
| Dextromethorphan Hydrobromide | 1.4842 |
| Directly Compressible Ascorbic Acid 97% | 9.2843 |
| Microcrystalline Cellulose NF | 14.6001 |
| Pregelatinized Starch, NF | 16.0591 |
| Stearic Acid, USP | 1.4589 |
| Magnesium Stearate | 0.4863 |
| Opadry II 57U93320 Orange | 2.0173 |
| Opadry FX62W32046 Yellow | 0.7204 |

Example 6 can be made by passing Phenylephrine HCl, Dextromethorphan HBr and Pregelatinized Starch through a 14 mesh screen and blend for 100 revolutions in a V-blender. Next, pass Ascorbic Acid and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press. Apply Opadry II 57U93320 Orange film coating using aqueous film-coating system to the composition. Then, apply Opadry FX62W32046 Yellow film coating using aqueous film-coating system.

Example 7

| Raw Material | % w/w |
| --- | --- |
| Directly Compressible Acetaminophen 90% | 53.1474 |
| Doxylamine Succinate USP | 0.9006 |
| Dextromethorphan Hydrobromide | 2.2262 |
| Directly Compressible Ascorbic Acid 97% | 18.5685 |
| Microcrystalline Cellulose NF | 9.5077 |
| Pregelatinized Starch, NF | 10.9667 |
| Stearic Acid, USP | 1.4589 |
| Magnesium Stearate | 0.4863 |
| Opadry II 57U91251 Green | 2.0173 |
| Opadry FX62W8547 Silver | 0.7204 |

Example 7 can be made by made by passing Doxylamine Succinate, Dextromethorphan HBr and Pregelatinized Starch through a 14 mesh screen and blend for 100 revolutions in a V-blender. Next, pass Ascorbic Acid and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press.

Apply Opadry II 57U91251 Green film coating using aqueous film-coating system to the composition. Then, apply Opadry FX62W8547 Silver film coating using aqueous film-coating system.

Example 8

| Raw Material | % w/w |
| --- | --- |
| Directly Compressible Acetaminophen 90% | 53.1113 |
| Phenylephrine Hydrochloride | 0.7781 |
| Dextromethorphan Hydrobromide | 1.4842 |
| Microcrystalline Cellulose NF | 14.6001 |
| Pregelatinized Starch, NF | 25.3434 |
| Stearic Acid, USP | 1.4589 |
| Magnesium Stearate | 0.4863 |
| Opadry II 57U93320 Orange | 2.0173 |
| Opadry FX62W32046 Yellow | 0.7204 |

Example 8 can be made by passing Phenylephrine HCl, Dextromethorphan HBr, and Pregelatinized Starch through a 14 mesh screen and blend for 100 revolutions in a V-blender. Next, pass Microcrystalline Cellulose through a 14 mesh screen into the pregelatinized starch mixture and blend for 100 revolutions. Next, Pass Acetaminophen and Stearic Acid through a 14 mesh screen into the pregelatinized mixture and blend for 100 revolutions. Next, Pass Magnesium Stearate through a 20 mesh screen into the pregelatinized mixture and blend for 30 revolutions to form the composition. Compress the composition on a tablet press. Apply Opadry II 57U93320 Orange film coating using aqueous film-coating system to the composition. Then, apply Opadry FX62W32046 Yellow film coating using aqueous film-coating system.

Example 9

| Raw Material | % w/w |
| --- | --- |
| Directly Compressible Acetaminophen 90% | 53.1474 |
| Doxylamine Succinate USP | 0.9006 |
| Dextromethorphan Hydrobromide | 2.2262 |
| Microcrystalline Cellulose NF | 9.5077 |
| Pregelatinized Starch, NF | 29.5352 |
| Stearic Acid, USP | 1.4589 |
| Magnesium Stearate | 0.4863 |
| Opadry II 57U91251 Green | 2.0173 |
| Opadry FX62W8547 Silver | 0.7204 |

Example 9 can be made by made by passing Doxylamine Succinate, Dextromethorphan HBr and Pregelatinized Starch through a 14 mesh screen and blend for 100 revolutions in a V-blender. Next, pass Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press. Apply Opadry II 57U91251 Green film coating using aqueous film-coating system to the composition. Then, apply Opadry FX62W8547 Silver film coating using aqueous film-coating system.

Example 10

| Raw Material | % w/w |
| --- | --- |
| Vitamin C | 25.00 |
| Pregelatinized Starch | 42.00 |
| Microcrystalline Cellulose | 30.0 |
| Stearic Acid | 3.0 |

Example 10 can be made by passing Vitamin C and Pregelatinized Starch through a 14 mesh screen and blend for 100 revolutions in a V-blender. Next, pass Microcrystalline Cellulose through a 14 mesh screen into the pregelatinized starch mixture and blend for 100 revolutions. Next, Pass Stearic Acid through a 20 mesh screen into the pregelatinized mixture and blend for 100 revolutions to form the composition. Compress the composition on a tablet press.

Example 11

| Raw Material | % w/w |
| --- | --- |
| Phenylephrine HCl | 5.0 |
| Pregelatinized Starch | 65.00 |
| Microcrystalline Cellulose | 27.0 |
| Stearic Acid | 3.0 |

Example 11 can be made by passing Phenylephrine HCl and Pregelatinized Starch through a 14 mesh screen and blend for 100 revolutions in a V-blender. Next, pass Microcrystalline Cellulose through a 14 mesh screen into the pregelatinized starch mixture and blend for 100 revolutions. Next, Pass Stearic Acid through a 20 mesh screen into the pregelatinized mixture and blend for 100 revolutions to form the composition. Compress the composition on a tablet press.

Example 12

| Raw Material | % W/W |
| --- | --- |
| Directly Compressible Acetaminophen 90% | 52.7560 |
| Phenylephrine Hydrochloride | 0.7500* |
| Dextromethorphan Hydrobromide | 1.4715** |
| Directly Compressible Ascorbic Acid 97% | 9.2047 |
| Microcrystalline Cellulose | 14.4750 |
| Pregelatinized Starch | 15.6804 |
| Stearic Acid | 1.9286 |
| Magnesium Stearate | 0.2410 |

-continued

| Raw Material | % W/W |
|---|---|
| Opadry II 85F1398 Orange | 2.8571 |
| Opadry FX 63F92532 Yellow | 0.7143 |

5% excess for manufacturing loss*
3% excess for manufacturing loss**

Example 12 can be made by passing Phenylephrine HCl, Dextromethorphan HBr and Pregelatinized Starch through a 14 mesh screen and blend for 100 revolutions in a V-blender. Next, pass Ascorbic Acid and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press. Apply Opadry II 85F1398 Orange film coating using aqueous film-coating system to the composition. Then, apply Opadry FX 63F92532 Yellow film coating using aqueous film-coating system.

Example 13

| Raw Material | % W/W |
|---|---|
| Directly Compressible Acetaminophen 90% | 52.7561 |
| Doxylamine Succinate | 0.8929 |
| Dextromethorphan Hydrobromide | 2.2071* |
| Directly Compressible Ascorbic Acid 97% | 18.4093 |
| Microcrystalline Cellulose | 9.4262 |
| Pregelatinized Starch | 10.6315 |
| Stearic Acid | 1.9286 |
| Magnesium Stearate | 0.2411 |
| Opadry II 85F1369 Green | 2.8571 |
| Opadry FX 63F97546 Silver | 0.7143 |

3% excess for manufacturing loss*

Example 13 can be made by made by passing Doxylamine Succinate, Dextromethorphan HBr and Pregelatinized Starch through a 14 mesh screen and blend for 100 revolutions in a V-blender. Next, pass Ascorbic Acid and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions. Next, Pass Magnesium Stearate through a 20 mesh screen into the pregelatinized mixture and blend for 30 revolutions to form the composition. Compress the composition on a tablet press. Apply Opadry II 85F1369 Green film coating using aqueous film-coating system to the composition. Then, apply Opadry FX 63F97546 Silver film coating using aqueous film-coating Example 14

| Raw Material | % W/W |
|---|---|
| Layer 1 | |
| Directly Compressible Acetaminophen 90% | 60.0649 |
| Directly Compressible Ascorbic Acid 97% | 20.2922 |
| Microcrystalline Cellulose | 17.0455 |
| Stearic Acid | 2.2727 |
| Magnesium Stearate | 0.3247 |
| Layer 2 | |
| Directly Compressible Acetaminophen 90% | 59.1054 |
| Pregelatinized Starch | 16.7732 |
| Microcrystalline Cellulose | 16.7732 |
| Phenylephrine Hydrochloride | 1.5974 |
| Dextromethorphan Hydrobromide | 3.1949 |
| Stearic Acid | 2.2364 |
| Magnesium Stearate | 0.3195 |

Example 14 can be made on a tablet press designed to produce two-layer tablets. Each layer is made separately, by the same process and steps described in Example 13. The individual layer compositions are then charged to separate hoppers of the two layer press. Layer 1 is compressed first and the powder for layer 2 then flows onto this pre-formed tablet, whereupon, layer 2 is compressed on top of the previously compressed layer 1.

Example 15

| Raw Material | % W/W |
|---|---|
| Directly Compressible Acetaminophen 90% | 52.7560 |
| Phenylephrine Hydrochloride | 0.7500* |
| Dextromethorphan Hydrobromide | 1.4715** |
| Ascorbic Acid/Eudragit coating | 9.2047 |
| Microcrystalline Cellulose | 14.4750 |
| Pregelatinized Starch | 15.6804 |
| Stearic Acid | 1.9286 |
| Magnesium Stearate | 0.2410 |
| Opadry II 85F1398 Orange | 2.8571 |
| Opadry FX 63F92532 Yellow | 0.7143 |

5% excess for manufacturing loss*
3% excess for manufacturing loss**

Example 15 can be made in a Wurster column, by spraying 3.0% of Eudragit L-30 onto a fluid bed of suspended ascorbic acid. The suspended ascorbic acid is encapsulated within a coating of the Euddragit L-30. Next the Phenylephrine HCl, Dextromethorphan HBr and Pregelatinized Starch is passed through a 14 mesh screen and blend for 100 revolutions in a V-blender. Next, pass Ascorbic Acid encapsulated within a Eudragit coating and Microcrystalline Cellulose through a 14 mesh screen into the pregelatinized starch mixture and blend for 100 revolutions. Pass Acetaminophen and Stearic Acid through a 14 mesh screen into pregelatinized mixture and blend for 100 revolutions.

Next, Pass Magnesium Stearate through a 20 mesh screen into the pregelatinized mixture and blend for 30 revolutions to form the composition. Compress the composition on a tablet press. Apply Opadry II 85F1398 Orange film coating using aqueous film-coating system to the composition. Then, apply Opadry FX 63F92532 Yellow film coating using aqueous film-coating system.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of achieving ingredient stabilization in an oral composition selected from the group consisting of compressed tablets, filled capsules, and two layered compressed tablets comprising the steps of:
    a) combining about 16.5%, by weight of the composition, pregelatinized starch with at least two sensitive ingredients wherein the sensitive ingredients comprise from about 5% to about 15%, by weight of the composition, ascorbic acid or a salt thereof and phenylephrine;
    b) adsorbing said sensitive ingredient onto the pregelatinized starch; and
    wherein said sensitive ingredient is evenly distributed throughout said pregelatinized starch.

2. The method of claim 1, said composition comprising from about 0.1% to about 20%, by weight of the composition, phenylephrine.

3. The method of claim 1, said composition comprising from about 0.5% to about 15%, by weight of the composition, phenylephrine.

4. The method of claim 1, further comprising the step of: encapsulating said sensitive ingredient within a coating.

5. The method of claim 1, further comprising the step of: forming a pre-blend.

6. The method of claim 5, further comprising the step of: diluting said pre-blend with at least one additional pharmaceutical active selected from the group consisting of acetaminophen, dextromethorphan, doxylamine, and combinations thereof.

7. The method of claim 1 further comprising from about 0.1% to 99% of an excipient, by weight of the composition.

8. The method of claim 7, wherein said excipient is selected from the group consisting of microcrystalline cellulose, dicalcium phosphate, stearic acid, magnesium stearate, corn starch, lactose, sodium croscarmellose, sodium starch glycolate, polyvinylpyrrolidone, gelatin and combinations thereof.

9. The method according to claim 1, wherein said composition is administered at least once weekly.

10. The method according to claim 1, wherein said composition is administered at least once monthly.

11. The method according to claim 1, wherein said composition is administered at least once daily.

12. The method of claim 1, wherein said composition further comprising a chelating agent.

13. A stable composition comprising about 16.5%, by weight of the composition, pregelatinized starch and at least two sensitive ingredients wherein the sensitive ingredients comprise from about 5% to about 15%, by weight of the composition, ascorbic acid or a salt thereof and phenylephrine; wherein said sensitive ingredients are adsorbed onto the pregelatinized starch; wherein said sensitive ingredients are evenly distributed throughout said pregelatinized starch therein to protect the sensitive ingredients from degradation by absorbing ambient moisture; and
    wherein said composition is an oral composition and said oral composition is selected from the group consisting of compressed tablets, filled capsules, and two layered compressed tablets.

14. The stable composition of claim 13, further comprising acetaminophen and dextromethorphan.

15. The stable composition of claim 13, further comprising from about 6% to about 25%, by weight of the composition, microcrystalline cellulose.

16. The stable composition of claim 13, further comprising stearic acid.

17. The stable composition of claim 13, wherein said composition is administered at least once weekly.

18. The stable composition of claim 13, wherein said composition is administered at least once monthly.

19. The stable composition of claim 13, wherein said composition is administered at least once daily.

20. The stable composition of claim 13, wherein said ascorbic acid is immediately released.

21. The stable composition of claim 13, further comprising magnesium stearate.

22. The stable composition of claim 13 wherein said composition is administered as-needed.

23. The stable composition of claim 13 wherein the oral composition is a compressed tablet.

24. The stable composition of claim 13 wherein the oral composition is a capsule.

25. A stable composition comprising:
    a. about 16.5%, by weight of the composition, pregelatinized starch;
    b. at least two sensitive ingredients wherein the sensitive ingredients comprise about 9.5%, by weight of the composition, ascorbic acid or a salt thereof and phenylephrine hydrochloride;
    c. about 15%, by weight of the composition, microcrystalline cellulose;
    d. acetaminophen;
    e. dextromethorphan;
    f. about 1.5%, by weight of the composition, stearic acid; and
    g. about 0.5%, by weight of the composition, magnesium stearate; wherein said sensitive ingredients are adsorbed onto the pregelatinized starch; wherein said sensitive ingredients are evenly distributed throughout said pregelatinized starch therein to protect the sensitive ingredients from degradation by absorbing ambient moisture; and
    wherein said composition is a compressed tablet.

* * * * *